US008718980B2

(12) United States Patent
Garudadri et al.

(10) Patent No.: US 8,718,980 B2
(45) Date of Patent: May 6, 2014

(54) METHOD AND APPARATUS FOR ARTIFACTS MITIGATION WITH MULTIPLE WIRELESS SENSORS

(75) Inventors: Harinath Garudadri, San Diego, CA (US); Pawan K. Baheti, San Diego, CA (US); Somdeb Majumdar, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 580 days.

(21) Appl. No.: 12/684,604

(22) Filed: Jan. 8, 2010

(65) Prior Publication Data

US 2011/0066381 A1    Mar. 17, 2011

Related U.S. Application Data

(60) Provisional application No. 61/241,851, filed on Sep. 11, 2009.

(51) Int. Cl.
*H03F 1/26* (2006.01)

(52) U.S. Cl.
USPC ........................................................ 702/189

(58) Field of Classification Search
USPC ........................................................ 702/189
See application file for complete search history.

(56) References Cited

U.S. PATENT DOCUMENTS

| 8,194,937 | B2 * | 6/2012 | Chen ............................ 382/118 |
| 2006/0029279 | A1 | 2/2006 | Donoho | |
| 2011/0022375 | A1 * | 1/2011 | Odille et al. ................... 703/13 |
| 2011/0044521 | A1 * | 2/2011 | Tewfik et al. ................. 382/131 |

FOREIGN PATENT DOCUMENTS

| CN | 1386252 A | 12/2002 |
| CN | 101107025 A | 1/2008 |
| EP | 1297784 A1 | 4/2003 |
| WO | WO2006075016 A1 | 7/2006 |
| WO | WO-2008057980 A2 | 5/2008 |
| WO | WO-2009031149 | 3/2009 |

OTHER PUBLICATIONS

Huang B Y, et al., "A pilot study on low power pulse rate detection based on compressive sampling", Engineering in Medicine and Biology Society, 2009. EMBC 2009. Annual International Conference of the IEEE, IEEE, Piscataway, NJ, USA, Sep. 3, 2009, pp. 753-756, XP031565453, ISBN: 978-1-4244-3296-7.

International Search Report and Written Opinion—PCT/US2010/048514—International Search Authority, European Patent Office,Jan. 19, 2011.

H. Garudadri and P.K. Baheti, "Packet loss mitigation for biomedical signals in healthcare telemetry," in Annual International Conference of the IEEE Engineering in Medicine and Biology Society (EMBC), pp. 2450-2453, Sep. 2009.

P.K. Baheti and H. Garudadri, "An ultra low power pulse oximeter sensor based on compressed sensing," in Sixth International Workshop on Wearable and Implantable Body Sensor Networks, pp. 144-148, Jun. 2009.

(Continued)

*Primary Examiner* — Aditya Bhat
(74) *Attorney, Agent, or Firm* — Dang M. Vo (57) ABSTRACT

Certain aspects of the present disclosure relate to a technique for mitigating artifacts of biophysical signals in a body area network. Information from multiple sensors (including motion information of the body) can be employed in mitigating the artifacts. The biophysical signals in the body area network can be compressively sensed.

40 Claims, 7 Drawing Sheets

(56) References Cited

OTHER PUBLICATIONS

F. S. Cettiveh and H. Garudadri, "Noninvasive cuffless estimation of blood pressure from pulse arrival time and heart rate with adaptive calibration," in Sixth International Workshop on Wearable and Implantable Body Sensor Networks, pp. 114-119, Jun. 2009.

E. Candes, J. Romberg, and T. Tao. "Stable signal recovery from incomplete and inaccurate measurements," in Communications on Pure and Applied Mathematics, vol. 59. pp. 1207-1223, Aug. 2006.

D. Donoho, "Compressed sensing." In IEEE Transactions on Biomedical Engineering, vol. 52, pp. 1289-1306, Apr. 2006.

* cited by examiner

METHOD AND APPARATUS FOR ARTIFACTS MITIGATION WITH MULTIPLE WIRELESS SENSORS

CLAIM OF PRIORITY UNDER 35 U.S.C. §119

The present Application for Patent claims benefit of Provisional Application Ser. No. 61/241,851 filed Sep. 11, 2009, and assigned to the assignee hereof and hereby expressly incorporated by reference herein.

BACKGROUND

1. Field

Certain aspects of the present disclosure generally relate to signal processing in wireless body area networks and, more particularly, to a method and an apparatus for mitigating artifacts by using multiple wireless sensors.

2. Background

Biophysical signals from a human body can be sensed by using various sensors such as: Ag/AgCl electrodes for sensing electro-cardiogram (ECG) signals, pulse oximeters for sensing blood oxygenation ($SpO_2$), micro-electro-mechanical (MEM) devices such as 3D-accelerometers for sensing physical activity, and so on. These signals can be then sent wirelessly to a body worn gateway device with connectivity to Wide Area Networks (WAN). It can be possible for automatic programs and/or healthcare providers to interpret vital signs from these biophysical signals, and to provide feedback to the user or intervene in therapy, as appropriate. In such applications, it is beneficial that the signals are free of sensing and transmission artifacts, as such artifacts can impede accurate interpretation.

There are algorithms in the art that perform artifact detection and removal. All of these algorithms detect anomalies in the biophysical signals and perform certain time-frequency domain operations to mitigate the impact of artifacts. However, the artifacts are removed directly in the signal space and not in a compressed sensing (CS) space. The CS may provide a lower implementation complexity, while accuracy of signal interpretation may be improved. For example, the CS acquisition may not produce aliasing due to high frequency components arising from motion and noise.

SUMMARY

Certain aspects provide a method for signal processing. The method generally includes generating sampling instances according to a random seed, sensing motion information, compressively sensing a first set of samples of a signal during the sampling instances, adjusting the sampling instances based on at least one of the sensed motion information or the sensed first set of samples, and compressively sensing a second set of samples of the signal during the adjusted sampling instances.

Certain aspects provide an apparatus for signal processing. The apparatus generally includes a first circuit configured to generate sampling instances according to a random seed, a sensor configured to sense motion information, another sensor configured to compressively sense a first set of samples of a signal during the sampling instances, and a second circuit configured to adjust the sampling instances based on at least one of the sensed motion information or the sensed first set of samples, wherein the other sensor is also configured to compressively sense a second set of samples of the signal during the adjusted sampling instances.

Certain aspects provide an apparatus for signal processing. The apparatus generally includes means for generating sampling instances according to a random seed, means for sensing motion information, means for compressively sensing a first set of samples of a signal during the sampling instances, means for adjusting the sampling instances based on at least one of the sensed motion information or the sensed first set of samples, and means for compressively sensing a second set of samples of the signal during the adjusted sampling instances.

Certain aspects provide a computer-program product for signal processing. The computer-program product includes a computer-readable medium comprising instructions executable to generate sampling instances according to a random seed, sense motion information, compressively sense a first set of samples of a signal during the sampling instances, adjust the sampling instances based on at least one of the sensed motion information or the sensed first set of samples, and compressively sense a second set of samples of the signal during the adjusted sampling instances.

Certain aspects provide a sensing device. The sensing device generally includes a first circuit configured to generate sampling instances according to a random seed, a sensor configured to sense motion information, another sensor configured to compressively sense a first set of samples of a signal during the sampling instances, a second circuit configured to adjust the sampling instances based on at least one of the sensed motion information or the sensed first set of samples, wherein the other sensor is also configured to compressively sense a second set of samples of the signal during the adjusted sampling instances, and a transmitter configured to transmit at least one of the sensed motion information or the sensed second set of samples.

Certain aspects provide a method for signal processing. The method generally includes receiving motion information and samples of a signal, generating a sparsity basis and a sensing matrix, determining at least one sparse space coefficient by using the sensing matrix, the sparsity basis and the received samples, modifying the at least one sparse space coefficient based on the motion information, and determining one or more other signals related to the received samples by using the at least one modified sparse space coefficient.

Certain aspects provide an apparatus for signal processing. The apparatus generally includes a receiver configured to receive motion information and samples of a signal, a first circuit configured to generate a sparsity basis and a sensing matrix, a computer configured to determine at least one sparse space coefficient by using the sensing matrix, the sparsity basis and the received samples, a second circuit configured to modify the at least one sparse space coefficient based on the motion information, and an estimator configured to determine one or more other signals related to the received samples by using the at least one modified sparse space coefficient.

Certain aspects provide an apparatus for signal processing. The apparatus generally includes means for receiving motion information and samples of a signal, means for generating a sparsity basis and a sensing matrix, means for determining at least one sparse space coefficient by using the sensing matrix, the sparsity basis and the received samples, means for modifying the at least one sparse space coefficient based on the motion information, and means for determining one or more other signals related to the received samples by using the at least one modified sparse space coefficient.

Certain aspects provide a computer-program product for signal processing. The computer-program product includes a computer-readable medium comprising instructions executable to receive motion information and samples of a signal, generate a sparsity basis and a sensing matrix, determine at least one sparse space coefficient by using the sensing matrix, the sparsity basis and the received samples, modify the at least one sparse space coefficient based on the motion information, and determine one or more other signals related to the received samples by using the at least one modified sparse space coefficient.

Certain aspects provide a headset. The headset generally includes a receiver configured to receive motion information and samples of a signal, a first circuit configured to generate a sparsity basis and a sensing matrix, a computer configured to determine at least one sparse space coefficient by using the sensing matrix, the sparsity basis and the received samples, a second circuit configured to modify the at least one sparse space coefficient based on the motion information, an estimator configured to determine one or more other signals related to the received samples by using the at least one modified sparse space coefficient, and a transducer configured to provide an audio output based on the determined one or more other signals.

Certain aspects provide a watch. The watch generally includes a receiver configured to receive motion information and samples of a signal, a first circuit configured to generate a sparsity basis and a sensing matrix, a computer configured to determine at least one sparse space coefficient by using the sensing matrix, the sparsity basis and the received samples, a second circuit configured to modify the at least one sparse space coefficient based on the motion information, an estimator configured to determine one or more other signals related to the received samples by using the at least one modified sparse space coefficient, and a user interface configured to provide an indication based on the determined one or more other signals.

Certain aspects provide a monitoring device. The monitoring device generally includes a connector, a receiver configured to receive via the connector motion information and samples of a signal, a first circuit configured to generate a sparsity basis and a sensing matrix, a computer configured to determine at least one sparse space coefficient by using the sensing matrix, the sparsity basis and the received samples, a second circuit configured to modify the at least one sparse space coefficient based on the motion information, an estimator configured to determine one or more other signals related to the received samples by using the at least one modified sparse space coefficient, and a user interface configured to provide an indication based on the determined one or more other signals.

BRIEF DESCRIPTION OF THE DRAWINGS

So that the manner in which the above-recited features of the present disclosure can be understood in detail, a more particular description, briefly summarized above, may be had by reference to aspects, some of which are illustrated in the appended drawings. It is to be noted, however, that the appended drawings illustrate only certain typical aspects of this disclosure and are therefore not to be considered limiting of its scope, for the description may admit to other equally effective aspects.

DETAILED DESCRIPTION

Various aspects of the disclosure are described more fully hereinafter with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the disclosure disclosed herein, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure, functionality, or structure and functionality in addition to or other than the various aspects of the disclosure set forth herein. It should be understood that any aspect of the disclosure disclosed herein may be embodied by one or more elements of a claim.

The word "exemplary" is used herein to mean "serving as an example, instance, or illustration." Any aspect described herein as "exemplary" is not necessarily to be construed as preferred or advantageous over other aspects.

Although particular aspects are described herein, many variations and permutations of these aspects fall within the scope of the disclosure. Although some benefits and advantages of the preferred aspects are mentioned, the scope of the disclosure is not intended to be limited to particular benefits, uses, or objectives. Rather, aspects of the disclosure are intended to be broadly applicable to different wireless technologies, system configurations, networks, and transmission protocols, some of which are illustrated by way of example in the figures and in the following description of the preferred aspects. The detailed description and drawings are merely illustrative of the disclosure rather than limiting, the scope of the disclosure being defined by the appended claims and equivalents thereof.

An Example Wireless Communication System

The techniques described herein may be used for various broadband wireless communication systems, including communication systems that are based on an orthogonal multiplexing scheme and a single carrier transmission. Examples of such communication systems include Orthogonal Frequency Division Multiple Access (OFDMA) systems, Single-Carrier Frequency Division Multiple Access (SC-FDMA) systems, Code Division Multiple Access (CDMA), and so forth. An OFDMA system utilizes orthogonal frequency division multiplexing (OFDM), which is a modulation technique that partitions the overall system bandwidth into multiple orthogonal sub-carriers. These sub-carriers may also be called tones, bins, etc. With OFDM, each sub-carrier may be independently modulated with data. An SC-FDMA system may utilize interleaved FDMA (IFDMA) to transmit on sub-carriers that are distributed across the system bandwidth, localized FDMA (LFDMA) to transmit on a block of adjacent sub-carriers, or enhanced FDMA (EFDMA) to transmit on multiple blocks of adjacent sub-carriers. In general, modulation symbols are sent in the frequency domain with OFDM and in the time domain with SC-FDMA. A CDMA system may utilize spread-spectrum technology and a coding scheme where each transmitter (i.e., user) is assigned a code in order to allow multiple users to be multiplexed over the same physical channel.

One specific example of a communication system based on an orthogonal multiplexing scheme is a WiMAX system. WiMAX, which stands for the Worldwide Interoperability for Microwave Access, is a standards-based broadband wireless technology that provides high-throughput broadband connections over long distances. There are two main applications of WiMAX today: fixed WiMAX and mobile WiMAX. Fixed WiMAX applications are point-to-multipoint, enabling broadband access to homes and businesses, for example. Mobile WiMAX offers the full mobility of cellular networks at broadband speeds.

IEEE 802.16x is an emerging standard organization to define an air interface for fixed and mobile broadband wireless access (BWA) systems. IEEE 802.16x approved "IEEE P802.16d/D5-2004" in May 2004 for fixed BWA systems and published "IEEE P802.16e/D12 Oct. 2005" in October 2005 for mobile BWA systems. The latest revision of the IEEE 802.16, "IEEE P802.16Rev2/D8 Dec. 2008", a draft standard, now consolidates materials from IEEE 802.16e and corrigendum. The standards define four different physical layers (PHYs) and one medium access control (MAC) layer. The OFDM and OFDMA physical layer of the four physical layers are the most popular in the fixed and mobile BWA areas respectively.

The teachings herein may be incorporated into (e.g., implemented within or performed by) a variety of wired or wireless apparatuses (e.g., nodes). In some aspects, a wireless node implemented in accordance with the teachings herein may comprise an access point or an access terminal.

An access terminal ("AT") may comprise, be implemented as, or known as an access terminal, a subscriber station, a subscriber unit, a mobile station, a remote station, a remote terminal, a user terminal, a user agent, a user device, user equipment, or some other terminology. In some implementations an access terminal may comprise a cellular telephone, a cordless telephone, a Session Initiation Protocol ("SIP") phone, a wireless local loop ("WLL") station, a personal digital assistant ("PDA"), a handheld device having wireless connection capability, or some other suitable processing device connected to a wireless modem. Accordingly, one or more aspects taught herein may be incorporated into a phone (e.g., a cellular phone or smart phone), a computer (e.g., a laptop), a portable communication device, a portable computing device (e.g., a personal data assistant), an entertainment device (e.g., a music or video device, or a satellite radio), a global positioning system device, or any other suitable device that is configured to communicate via a wireless or wired medium. In some aspects the node is a wireless node. Such wireless node may provide, for example, connectivity for or to a network (e.g., a wide area network such as the Internet or a cellular network) via a wired or wireless communication link.

Figure 1:
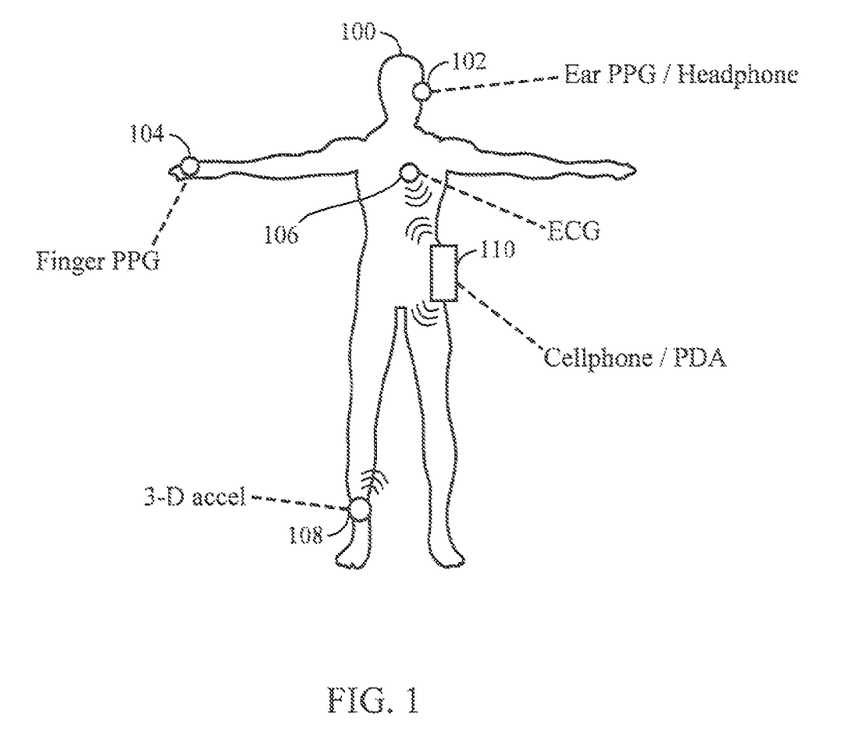
FIG. 1 illustrates an example of a body area network (BAN) in accordance with certain aspects of the present disclosure.

Certain aspects of the present disclosure support methods implemented in body area networks (BANs). The BANs represent promising concept for healthcare applications such as continuous monitoring for diagnostic purposes, effects of medicines on chronic ailments, and alike. FIG. 1 illustrates an example of a BAN 100 that may comprise several acquisition circuits 102-108. Each acquisition circuit may comprise wireless sensor that senses one or more vital biophysical signals and communicates them (e.g., over a wireless channel) to an aggregator 110 for processing purposes.

The BAN 100 may be therefore viewed as a wireless communication system where various wireless nodes (i.e., acquisition circuits and aggregator) communicate using either orthogonal multiplexing scheme or a single carrier transmission. The aggregator 110 may be a mobile handset, a wireless watch, a headset, a monitoring device, or a Personal Data Assistant (PDA). As illustrated in FIG. 1, an acquisition circuit 102 may correspond to an ear photoplethysmograph (PPG) sensor, an acquisition circuit 104 may correspond to a finger PPG sensor, an acquisition circuit 106 may correspond to an electro-cardiogram (ECG) sensor, and an acquisition circuit 108 may correspond to a 3D-Accelerometer (3D-Accl) sensor.

Figure 2:
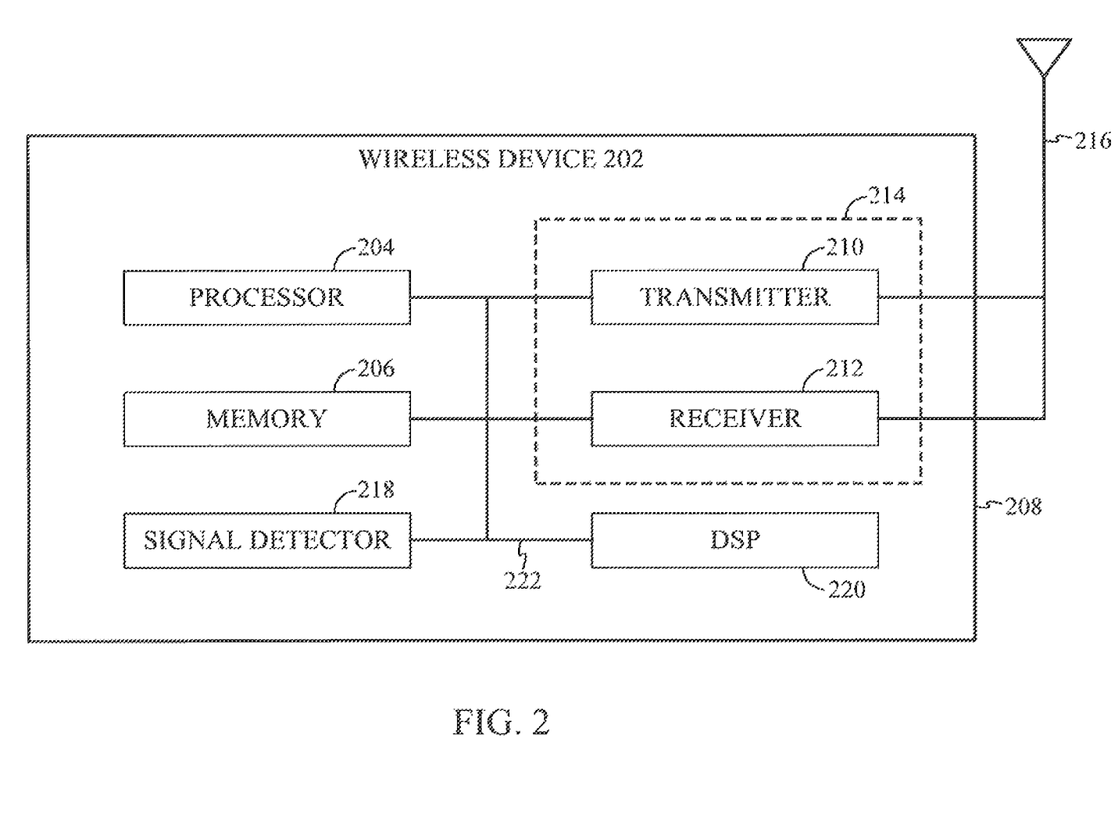
FIG. 2 illustrates various components that may be utilized in a wireless device of the BAN in accordance with certain aspects of the present disclosure.

FIG. 2 illustrates various components that may be utilized in a wireless device 202 that may be employed within the BAN 100. The wireless device 202 is an example of a device that may be configured to implement the various methods described herein. The wireless device 202 may correspond to the aggregator 110 or to one of the acquisition circuits 102-108.

The wireless device 202 may include a processor 204 which controls operation of the wireless device 202. The processor 204 may also be referred to as a central processing unit (CPU). Memory 206, which may include both read-only memory (ROM) and random access memory (RAM), provides instructions and data to the processor 204. A portion of the memory 206 may also include non-volatile random access memory (NVRAM). The processor 204 typically performs logical and arithmetic operations based on program instructions stored within the memory 206. The instructions in the memory 206 may be executable to implement the methods described herein.

The wireless device 202 may also include a housing 208 that may include a transmitter 210 and a receiver 212 to allow transmission and reception of data between the wireless device 202 and a remote location. The transmitter 210 and receiver 212 may be combined into a transceiver 214. An antenna 216 may be attached to the housing 208 and electrically coupled to the transceiver 214. The wireless device 202 may also include (not shown) multiple transmitters, multiple receivers, multiple transceivers, and/or multiple antennas.

The wireless device 202 may also include a signal detector 218 that may be used in an effort to detect and quantify the level of signals received by the transceiver 214. The signal detector 218 may detect such signals as total energy, energy per subcarrier per symbol, power spectral density and other signals. The wireless device 202 may also include a digital signal processor (DSP) 220 for use in processing signals.

The various components of the wireless device 202 may be coupled together by a bus system 222, which may include a power bus, a control signal bus, and a status signal bus in addition to a data bus.

Mitigation of Biophysical Signal Artifacts Using Multiple Sensors

Novel approach for mitigating signal artifacts in biophysical signals is proposed in the present disclosure where information from multiple sensors (including motion information of a body) is employed. The biophysical signals of a body area network (BAN) (e.g., the BAN 100 illustrated in FIG. 1) may be sensed in a compressive manner with a sampling frequency lower than the Nyquist frequency.

In the BAN 100, the 3D-Accelerometer (3D-Accl) sensor 108 may be co-located along with the pulse oximeter sensor, such as the ear photoplethysmograph (PPG) sensor 102 or the finger PPG sensor 104. Then, motion of the PPG sensor may be directly inferred from the 3D-Accl data. Based on the inferred motion information, motion artifacts of the sensed PPG data may be mitigated.

In one aspect of the present disclosure, a mapping function may be built between the motion information and the PPG data artifacts. Models of motion and noise artifacts may be constructed in the compressed sensing (CS) reconstruction space rather than in the given signal space. It should be noted that aliasing due to high frequency components arising from motion and noise may not be produced during the CS acquisition, which may result into improved accuracy of signal interpretation.

At the reconstruction side, one or more of the spectral components such as noise components predicted by the mapping function may be set to zero, thereby mitigating noise artifacts directly in the CS reconstruction domain. Furthermore, one or more spectral components may be modified based on values predicted by a motion model, thereby mitigating motion artifacts directly in the CS reconstruction domain. In addition, the information from motion sensors may be used to adapt the CS acquisition in order to enhance robustness to acquisition errors.

Figure 3:
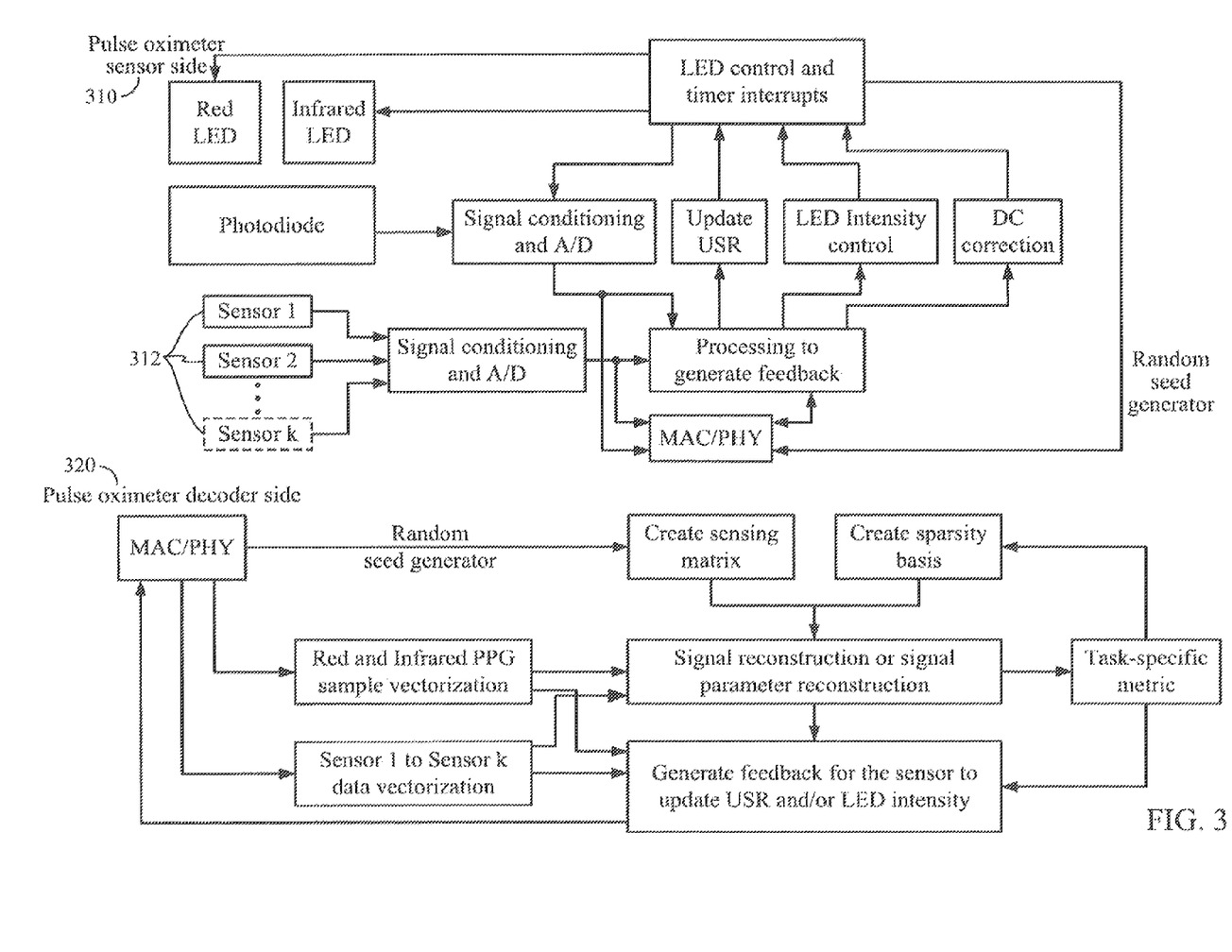
FIG. 3 illustrates an example of generalized pulse oximeter sensor side and an example of generalized pulse oximeter decoder side in accordance with certain aspects of the present disclosure.

FIG. 3 illustrates an example of generalized pulse oximeter sensor side 310 and an example of generalized pulse oximeter decoder side 320 in accordance with certain aspects of the present disclosure. In one aspect of the present disclosure, 3D-Accl data may be processed at the pulse oximeter sensor side 310 and used to modify PPG sensing parameters, so that motion artifacts may be minimized in sensing of the PPG signals. In another aspect of the present disclosure, the sensing parameters of at least one sensor 312 of the pulse oximeter 310 may be estimated at the pulse oximeter decoder 320 based on information received from another sensor 312. In another aspect of the present disclosure, information from at least one of the sensors 312 may be processed to mitigate acquisition artifacts based on samples from at least one more sensor 312. In yet another aspect of the present disclosure, at least one of the sensors 312 may be compressively sampled and data from all the sensors 312 may be transmitted to the receiver 320 for further processing.

Figure 4:
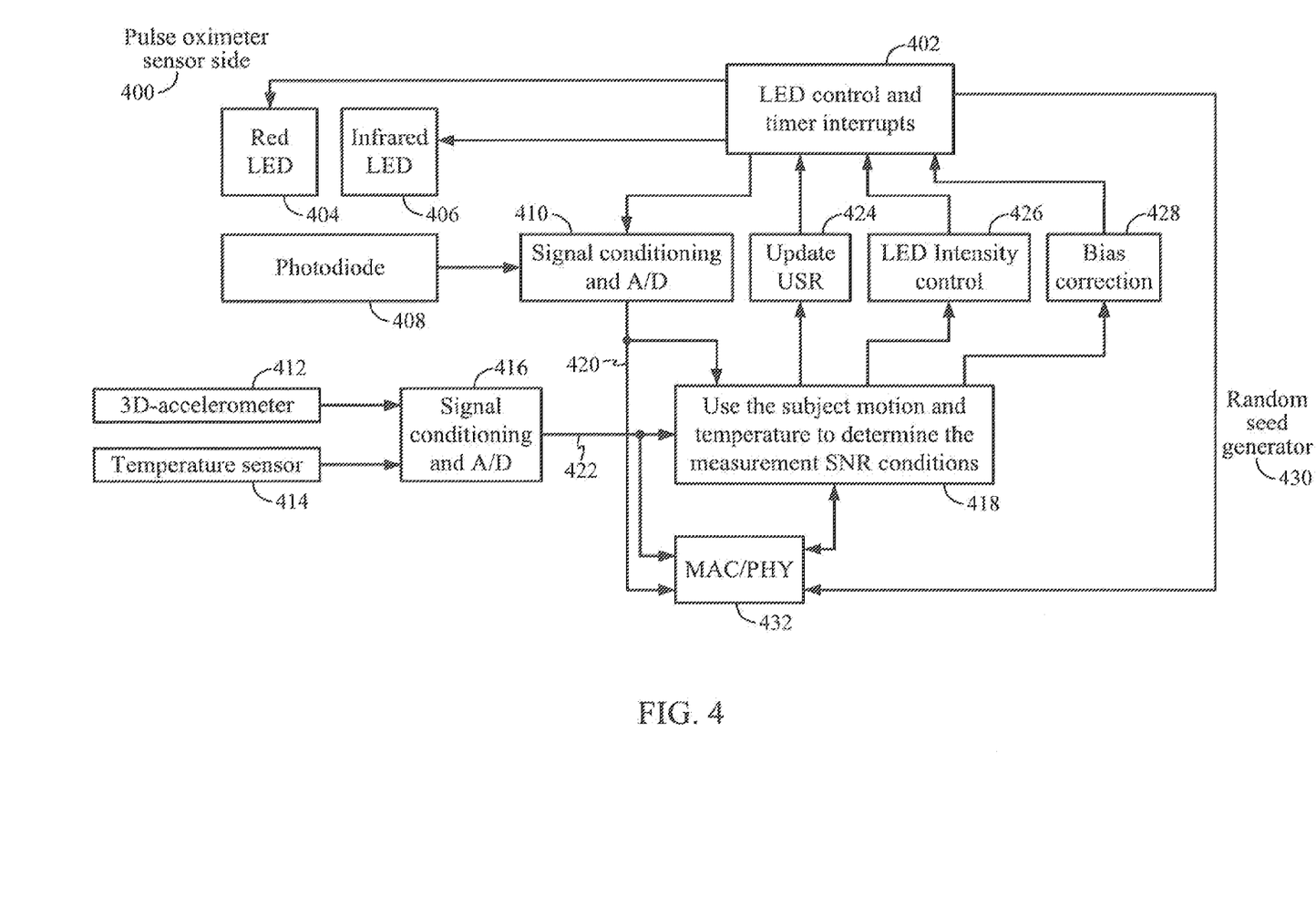
FIG. 4 illustrates an example of pulse oximeter sensor side with multiple sensors in accordance with certain aspects of the present disclosure.

FIG. 4 illustrates an example of a pulse oximeter sensor side 400 equipped with multiple sensors in accordance with certain aspects of the present disclosure. Light-emitting diode (LED) control and timer interrupts module 402 may control the lighting of red LEDs 404 and of infrared (IR) LEDs 406, as well as their intensity levels. The module 402 may also provide sampling instances to a signal conditioning block 410 associated with a photodiode 408. The sampling instances may be generated according to a sampling frequency lower than the Nyquist frequency, which corresponds to the CS acquisition. The ratio of the Nyquist frequency to the frequency of CS acquisition represents the under-sampling ratio (USR).

A 3D-accelerometer 412 and temperature sensors 414 may be used to provide feedback through a signal conditioning block 416, such that measurement signal-to-noise ratio (SNR) conditions may be determined by unit 418. The sampled data 420 from the photodiode 408 may be decomposed into two vectors corresponding to red and IR LEDs. These vectors are denoted as under-sampled Red PPG and under-sampled IR PPG samples, respectively.

The PPG samples 420 and sensory data 422 associated with the 3D-accelerometer 412 and temperature sensors 414 may be processed in the unit 418 for updating a USR in unit 424, generating LED intensity control in unit 426 if the SNR is below a defined threshold value, and computing in unit 428 a correction of bias of every sensed signal in case when the photodiode measurement is drifting due to ambient light, motion, and alike. It can be observed from FIG. 4 that a random seed generator value 430 may be used (along with the updated USR, the LED intensity control and the bias correction) for generating the LED timer interrupts.

The sensory data 422, the PPG samples 420 and the random seed generator value 430 may be packetized and transferred to a Media Access Control/Physical layer (MAC/PHY) 432 for transmission to a reconstruction side, such as the pulse oximeter decoder side 320 illustrated in FIG. 3. The packetizing may be performed such that samples corrupted during the transmission can be efficiently reconstructed at the decoder side. Moreover, not all packets of samples may need to be transmitted to the reconstruction side. Instead, a reduced set of packets may be transmitted, for example in case of favorable channel conditions or for the purpose of saving transmission power. Those samples that belong to packets not being transmitted may be reconstructed at the decoder side using the received packets.

The pulse oximeter sensor side 400 may be also capable to receive feedback information from the reconstruction side. The feedback information may comprise at least one of: an update of the USR, information about a lighting intensity of the one or more LEDs, or the correction of bias. The sampling instances may be adjusted based on the received feedback information.

Figure 5:
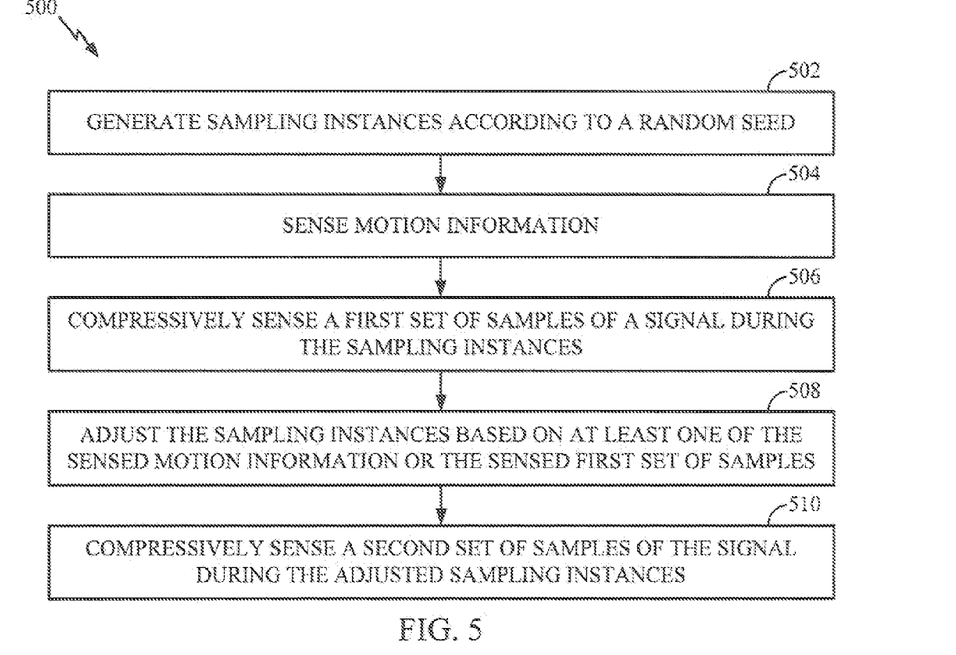
FIG. 5 illustrates example operations that may be performed at the pulse oximeter sensor side in accordance with certain aspects of the present disclosure.

FIG. 5 illustrates example operations 500 that may be performed at the pulse oximeter sensor side 400 in accordance with certain aspects of the present disclosure. At 502, sampling instances may be generated according to a random seed. At 504, motion information may be sensed. At 506, a first set of samples of a signal (e.g., an electro-cardiogram (ECG) signal, a PPG signal, or both) may be compressively sensed during the sampling instances. At 508, the sampling instances may be adjusted based on at least one of the sensed motion information or the sensed first set of samples. At 510, a second set of samples of the signal may be compressively sensed during the adjusted sampling instances. It should be noted that, beside the PPG and ECG data, the motion information may be also compressively sensed.

Figure 6:
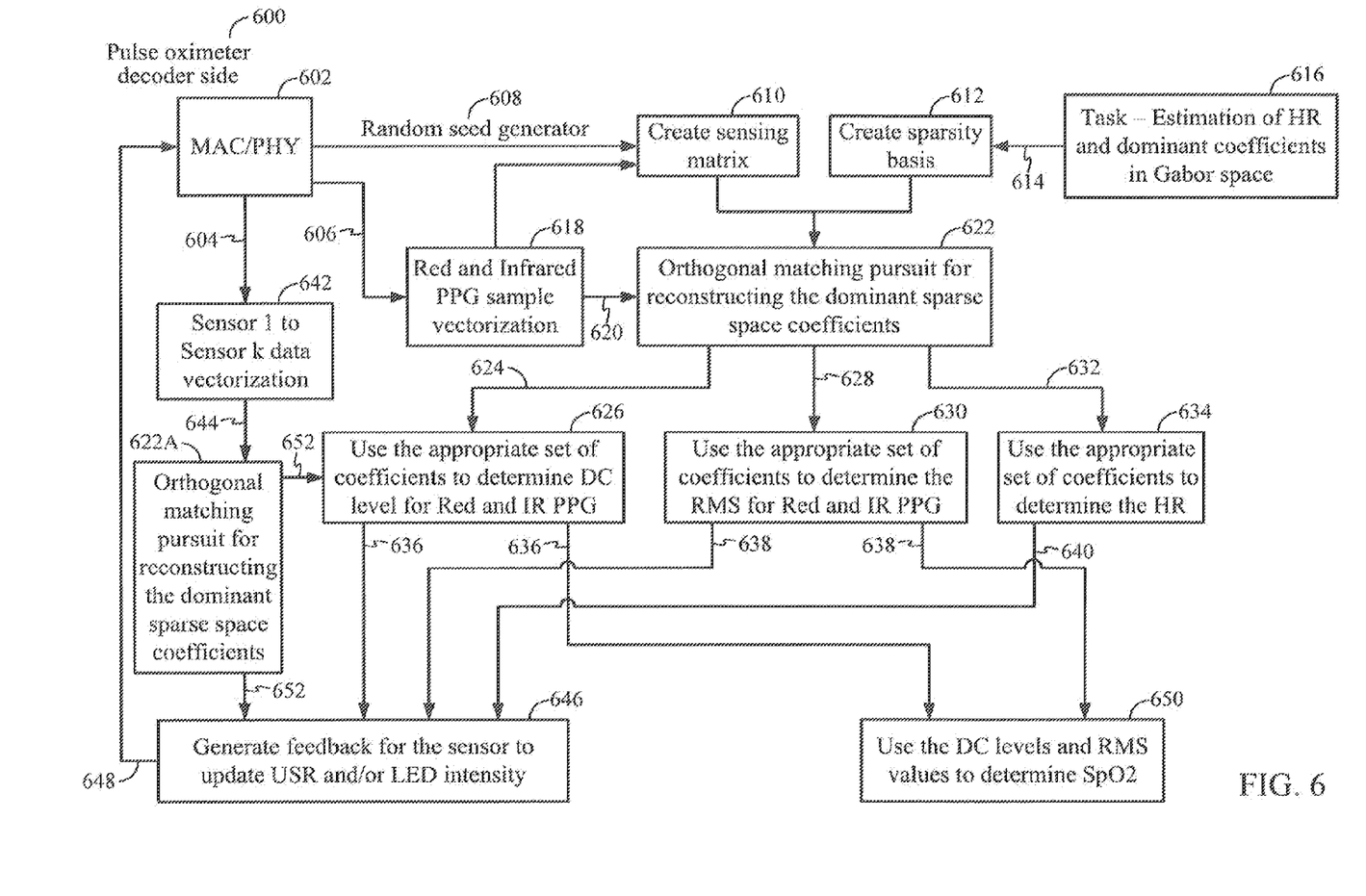
FIG. 6 illustrates an example of pulse oximeter decoder side in accordance with certain aspects of the present disclosure.

FIG. 6 illustrates an example of a pulse oximeter decoder side 600 in accordance with certain aspects of the present disclosure. Sensory data 604 and PPG samples 606 may be extracted from received packetized data that were transmitted from the pulse oximeter sensor side 400. A random seed generator value 608 received from a MAC/PHY 602 may be used by unit 610 to determine a sensing matrix. The sparsity basis may be created by unit 612 based on an indication 614 about a task of interest. The task of interest may be, for example, related to estimation of a heart rate and to extraction of dominant coefficients in the Gabor space, and it may be determined by unit 616.

By using the generated sensing matrix, the created sparsity basis, and estimated red and infrared (IR) PPG waveforms 620 from a sample vectorization unit 618, the dominant coefficients in the sparse space may be determined in unit 622 according to the orthogonal matching pursuit approach. It should be noted that the sparse space coefficients may contain contributions from the noise artifacts. The determination of these coefficients may also comprise identification of the coefficients in the sparse space based on statistical hypothesis testing approaches, which may utilize a priori statistical information about noise sources. Appropriate set of sparse space coefficients 624 from the estimated red and IR PPG waveforms 620 may be utilized by unit 626 to determine DC levels 636 of the red and IR PPG signals. Furthermore, motion information 652 (i.e., dominant coefficients in the sparse space determined by unit 622A based on sensory data 644 from a data vectorization unit 642) may be utilized to modify the red and IR PPG waveforms 624 in the sparse space prior to additional estimations performed by the unit 626. Appropriate set of sparse space coefficients 628 from the estimated red and IR PPG waveforms 620 may be utilized by unit 630 to determine RMS levels 638 of the red and IR PPG signals. Furthermore, appropriate set of sparse space coefficients 632 from the estimated red and IR PPG waveforms 620 may be utilized by unit 634 to determine a heart rate (HR) 640.

At least one of: the DC levels 636, the RMS levels 638, the HR estimate 640 or the motion information 652 may be utilized by unit 646 to generate feedback information 648 for the pulse oximeter sensor 400. The feedback information may comprise at least one of: an update of the USR, information about a lighting intensity of the LEDs of the sensor 400, or a DC level correction (i.e., a bias correction) of each sensed signal. The feedback information may be utilized for adjusting the sampling instances at the pulse oximeter sensor 400. In addition, blood oxygenation ($SpO_2$) levels may be estimated in unit 650 by using the DC levels 636 and the RMS levels 638 of red and IR PPG signals. At least one of the determined HR, the estimated blood oxygenation levels, the red and IR PPG waveforms, or the ECG waveform may be modified based on the motion information.

Figure 7:
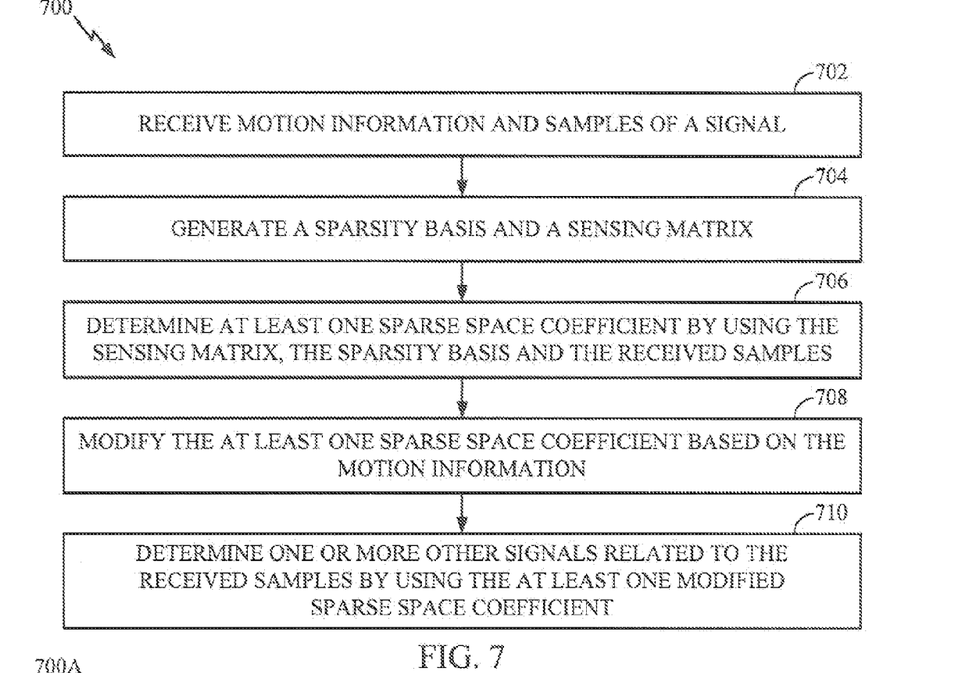
FIG. 7 illustrates example operations that may be performed at the pulse oximeter decoder side in accordance with certain aspects of the present disclosure.

FIG. 7 illustrates example operations 700 that may be performed at the pulse oximeter decoder side in accordance with certain aspects of the present disclosure. At 702, motion information transmitted from the sensor side 400 may be received at the decoder 600, as well as samples of a biomedical signal, such as at least one of the PPG signal or the ECG signal. At 704, a sparsity basis and a sensing matrix may be generated. At 706, at least one sparse space coefficient may be computed by using the sensing matrix, the sparsity basis and the received samples. At 708, the at least one sparse space coefficient may be modified based on the motion information. The modification may comprise setting the at least one sparse space coefficient to zero, for example the coefficient associated with 50 Hz or 60 Hz interference. At 710, one or more other signals related to the received samples of the signal may be determined by using the at least one modified sparse space coefficient.

Figure 5A:
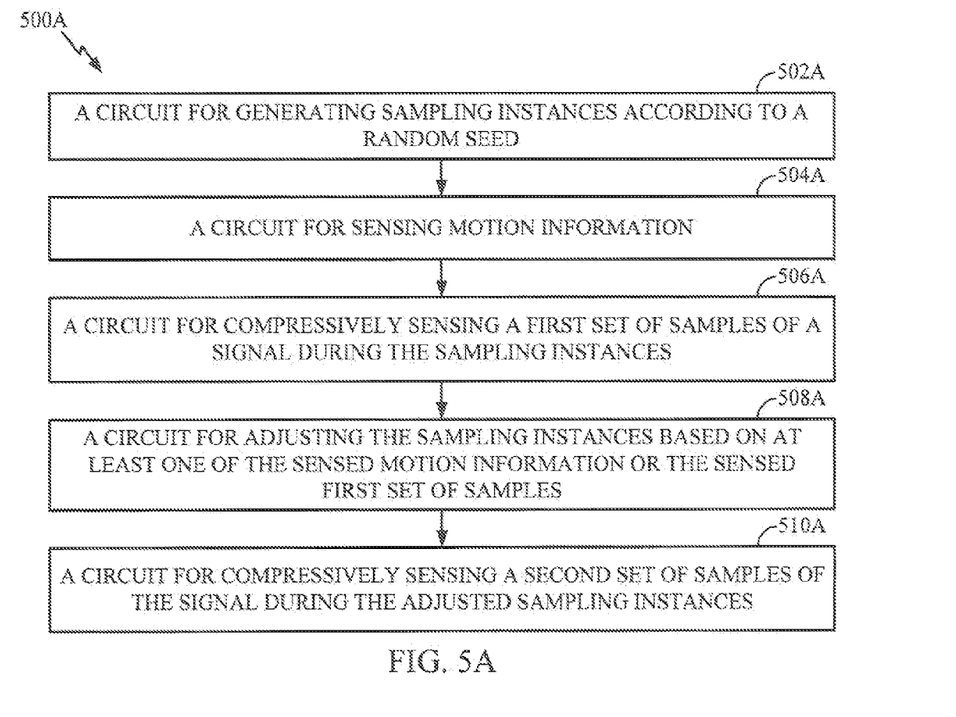
FIG. 5A illustrates example components capable of performing the operations illustrated in FIG. 5.
Figure 7A:
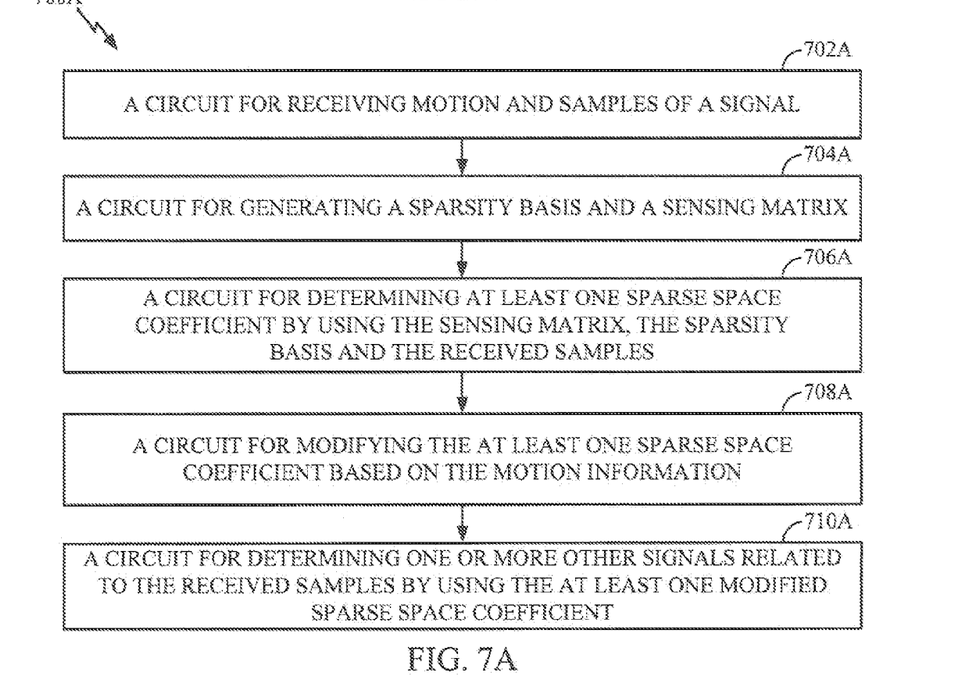
FIG. 7A illustrates example components capable of performing the operations illustrated in FIG. 7.

The various operations of methods described above may be performed by any suitable means capable of performing the corresponding functions. The means may include various hardware and/or software component(s) and/or module(s), including, but not limited to a circuit, an application specific integrate circuit (ASIC), or processor. Generally, where there are operations illustrated in Figures, those operations may have corresponding counterpart means-plus-function components with similar numbering. For example, operations 500 and 700, illustrated in FIGS. 5 and 7 correspond to components 500A and 700A illustrated in FIGS. 5A and 7A.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various operations of methods described above may be performed by any suitable means capable of performing the operations, such as various hardware and/or software component(s), circuits, and/or module(s). Generally, any operations illustrated in the Figures may be performed by corresponding functional means capable of performing the operations.

The various illustrative logical blocks, modules and circuits described in connection with the present disclosure may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the present disclosure may be embodied directly in hardware, in a software module executed by a processor, or in a combination of the two. A software module may reside in any form of storage medium that is known in the art. Some examples of storage media that may be used include random access memory (RAM), read only memory (ROM), flash memory, EPROM memory, EEPROM memory, registers, a hard disk, a removable disk, a CD-ROM and so forth. A software module may comprise a single instruction, or many instructions, and may be distributed over several different code segments, among different programs, and across multiple storage media. A storage medium may be coupled to a processor such that the processor can read information from, and write information to, the storage medium. In the alternative, the storage medium may be integral to the processor.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

The functions described may be implemented in hardware, software, firmware or any combination thereof. If implemented in software, the functions may be stored as one or more instructions on a computer-readable medium. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray® disc where disks usually reproduce data magnetically, while discs reproduce data optically with lasers.

Thus, certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

A wireless device in the present disclosure may include various components that perform functions based on signals that are transmitted by or received at the wireless device. A wireless device may also refer to a wearable wireless device. In some aspects the wearable wireless device may comprise a wireless headset or a wireless watch. For example, a wireless headset may include a transducer adapted to provide audio output based on data received via a receiver. A wireless watch may include a user interface adapted to provide an indication based on data received via a receiver. A wireless sensing device may include a sensor adapted to provide data to be transmitted via a transmitter.

A wireless device may communicate via one or more wireless communication links that are based on or otherwise support any suitable wireless communication technology. For example, in some aspects a wireless device may associate with a network. In some aspects the network may comprise a personal area network (e.g., supporting a wireless coverage area on the order of 30 meters) or a body area network (e.g., supporting a wireless coverage area on the order of 10 meters) implemented using ultra-wideband technology or some other suitable technology. In some aspects the network may comprise a local area network or a wide area network. A wireless device may support or otherwise use one or more of a variety of wireless communication technologies, protocols, or standards such as, for example, CDMA, TDMA, OFDM, OFDMA, WiMAX, and Wi-Fi. Similarly, a wireless device may support or otherwise use one or more of a variety of corresponding modulation or multiplexing schemes. A wireless device may thus include appropriate components (e.g., air interfaces) to establish and communicate via one or more wireless communication links using the above or other wireless communication technologies. For example, a device may comprise a wireless transceiver with associated transmitter and receiver components (e.g., transmitter 210 and receiver 212) that may include various components (e.g., signal generators and signal processors) that facilitate communication over a wireless medium.

The teachings herein may be incorporated into (e.g., implemented within or performed by) a variety of apparatuses (e.g., devices). For example, one or more aspects taught herein may be incorporated into a phone (e.g., a cellular phone), a personal data assistant ("PDA") or so-called smart-phone, an entertainment device (e.g., a portable media device, including music and video players), a headset (e.g., headphones, an earpiece, etc.), a microphone, a medical sensing device (e.g., a biometric sensor, a heart rate monitor, a pedometer, an EKG device, a smart bandage, etc.), a user I/O device (e.g., a watch, a remote control, a light switch, a keyboard, a mouse, etc.), an environment sensing device (e.g., a tire pressure monitor), a monitoring device that may receive data from the medical or environment sensing device (e.g., a desktop, a mobile computer, etc.), a point-of-care device, a hearing aid, a set-top box, or any other suitable device. The monitoring device may also have access to data from different sensing devices via connection with a network.

These devices may have different power and data requirements. In some aspects, the teachings herein may be adapted for use in low power applications (e.g., through the use of an impulse-based signaling scheme and low duty cycle modes) and may support a variety of data rates including relatively high data rates (e.g., through the use of high-bandwidth pulses).

In some aspects a wireless device may comprise an access device (e.g., an access point) for a communication system. Such an access device may provide, for example, connectivity to another network (e.g., a wide area network such as the Internet or a cellular network) via a wired or wireless communication link. Accordingly, the access device may enable another device (e.g., a wireless station) to access the other network or some other functionality. In addition, it should be appreciated that one or both of the devices may be portable or, in some cases, relatively non-portable. Also, it should be appreciated that a wireless device also may be capable of transmitting and/or receiving information in a non-wireless manner (e.g., via a wired connection) via an appropriate communication interface.

While the foregoing is directed to aspects of the present disclosure, other and further aspects of the disclosure may be devised without departing from the basic scope thereof, and the scope thereof is determined by the claims that follow.

The invention claimed is:

1. A method for signal processing, comprising:
   receiving, by an apparatus, samples of a signal from a sensor;
   receiving, by the apparatus, information related to a motion of the sensor;
   generating, by the apparatus, a sparsity basis and a sensing matrix;
   determining, by the apparatus, at least one sparse space coefficient by using the sensing matrix, the sparsity basis and the received samples;
   modifying, by the apparatus, the at least one sparse space coefficient based on the motion information to mitigate artifacts present in the at least one sparse space coefficient due to the motion of the sensor; and
   determining, by the apparatus, one or more other signals related to the received samples by using the at least one modified sparse space coefficient.

2. The method of claim 1, further comprising:
   generating, based on at least one of the determined one or more other signals or the motion information, feedback information for adjusting sensing at an apparatus of at least one of other samples of the signal or other motion information, the other samples and the other motion information to be received from the apparatus; and
   transmitting the generated feedback information to the apparatus.

3. The method of claim 2, wherein the feedback information comprises at least one of: an update of an under-sampling ratio (USR) information about a lighting intensity of light-emitting diodes (LEDs), or a correction of DC component of the signal.

4. The method of claim 1, wherein the signal comprises at least one of: a red photoplethysmograph (PPG) signal, an infrared (IR) PPG signal, or an electro-cardiogram (ECG) signal.

5. The method of claim 4, wherein the determined one or more other signals comprise at least one of: a DC component, a root mean square (RMS) component, or a waveform.

6. The method of claim 1, further comprising
   modifying, based on the motion information, at least one of: a determined level of oxygenation in blood, a determined heart rate, a red photoplethysmograph (PPG) signal, an infrared (IR) PPG signal, an electro-cardiogram (ECG) signal, or the one or more other signals;
   wherein the one or more other signals comprise at least one of: a DC component, a root mean square (RMS) component, or a waveform.

7. The method of claim 1, wherein the at least one sparse space coefficient is determined according to the orthogonal matching pursuit algorithm.

8. The method of claim 1, further comprising
   providing, based on the determined one or more other signals, an indication of at least one of: a heart rate, a level of blood oxygenation, a photoplethysmograph (PPG) signal, or an electro-cardiogram (ECG) signal.

9. The method of claim 1, wherein the modification comprises:
   setting the at least one sparse space coefficient to zero.

10. The method of claim 1, further comprising:
    receiving one or more packets comprising at least one of a corrupted version of the motion information or a corrupted version of the samples; and
    reconstructing at least one of the motion information or the samples using the one or more packets.

11. The method of claim 1, wherein determining the at least one sparse space coefficient further comprises:
    identifying the at least one sparse space coefficient based on a priori statistical information about noise sources.

12. An apparatus for signal processing, comprising:
    a receiver configured to:
        receive samples of a signal from a sensor; and
        receive information related to a motion of the sensor;
    a first circuit configured to generate a sparsity basis and a sensing matrix;
    a computer configured to determine at least one sparse space coefficient by using the sensing matrix, the sparsity basis and the received samples;
    a second circuit configured to modify the at least one sparse space coefficient based on the motion information to mitigate artifacts present in the at least one sparse space coefficient due to the motion of the sensor; and
    an estimator configured to determine one or more other signals related to the received samples by using the at least one modified sparse space coefficient.

13. The apparatus of claim 12, further comprising:
    a third circuit configured to generate, based on at least one of the determined one or more other signals or the motion information, feedback information for adjusting sensing at another apparatus of at least one of other samples of the signal or other motion information, the other samples and the other motion information to be received from the other apparatus; and
    a transmitter configured to transmit the generated feedback information to the other apparatus.

14. The apparatus of claim 13, wherein the feedback information comprises at least one of: an update of an under-sampling ratio (USR) information about a lighting intensity of light-emitting diodes (LEDs), or a correction of DC component of the signal.

15. The apparatus of claim 12, wherein the signal comprises at least one of: a red photoplethysmograph (PPG) signal, an infrared (IR) PPG signal, or an electro-cardiogram (ECG) signal.

16. The apparatus of claim 15, wherein the determined one or more other signals comprise at least one of: a DC component, a root mean square (RMS) component, or a waveform.

17. The apparatus of claim 12, further comprising
    a third circuit configured to modify, based on the motion information, at least one of a determined level of oxygenation in blood, a determined heart rate, a red photoplethysmograph (PPG) signal, an infrared (IR) PPG signal, an electro-cardiogram (ECG) signal, or the one or more other signals;
    wherein the one or more other signals comprise at least one of: a DC component, a root mean square (RMS) component, or a waveform.

18. The apparatus of claim 12, wherein the at least one sparse space coefficient is determined according to the orthogonal matching pursuit algorithm.

19. The apparatus of claim 12, further comprising
    a third circuit configured to provide, based on the determined one or more other signals, an indication of at least one of: a heart rate, a level of blood oxygenation, a photoplethysmograph (PPG) signal, or an electro-cardiogram (ECG) signal.

20. The apparatus of claim 12, wherein the second circuit is also configured to set the at least one sparse space coefficient to zero.

21. The apparatus of claim 12, wherein
    the receiver is also configured to receive one or more packets comprising at least one of a corrupted version of the motion information or a corrupted version of the samples, and the apparatus further comprising a reconstructing circuit configured to reconstruct at least one of the motion information or the samples using the one or more packets.

22. The apparatus of claim 12, wherein the computer is also configured to identify the at least one sparse space coefficient based on a priori statistical information about noise sources.

23. An apparatus for signal processing, comprising:
means for receiving samples of a signal from a sensor and information related to a motion of the sensor;
means for generating a sparsity basis and a sensing matrix;
means for determining at least one sparse space coefficient by using the sensing matrix, the sparsity basis and the received samples;
means for modifying the at least one sparse space coefficient based on the motion information to mitigate artifacts present in the at least one sparse space coefficient due to the motion of the sensor; and
means for determining one or more other signals related to the received samples by using the at least one modified sparse space coefficient.

24. The apparatus of claim 23, further comprising:
means for generating, based on at least one of the determined one or more other signals or the motion information, feedback information for adjusting sensing at another apparatus of at least one of other samples of the signal or other motion information, the other samples and the other motion information to be received from the other apparatus; and
means for transmitting the generated feedback information to the other apparatus.

25. The apparatus of claim 24, wherein the feedback information comprises at least one of: an update of an undersampling ratio (USR) information about a lighting intensity of light-emitting diodes (LEDs), or a correction of DC component of the signal.

26. The apparatus of claim 23, wherein the signal comprises at least one of: a red photoplethysmograph (PPG) signal, an infrared (IR) PPG signal, or an electro-cardiogram (ECG) signal.

27. The apparatus of claim 26, wherein the determined one or more other signals comprise at least one of: a DC component, a root mean square (RMS) component, or a waveform.

28. The apparatus of claim 23, further comprising
means for modifying, based on the motion information, at least one of: a determined level of oxygenation in blood, a determined heart rate, a red photoplethysmograph (PPG) signal, an infrared (IR) PPG signal, an electro-cardiogram (ECG) signal, or the one or more other signals;
wherein the one or more other signals comprise at least one of: a DC component, a root mean square (RMS) component, or a waveform.

29. The apparatus of claim 23, wherein the at least one sparse space coefficient is determined according to the orthogonal matching pursuit algorithm.

30. The apparatus of claim 23, further comprising
means for providing, based on the determined one or more other signals, an indication of at least one of: a heart rate, a level of blood oxygenation, a photoplethysmograph (PPG) signal, or an electro-cardiogram (ECG) signal.

31. The apparatus of claim 23, wherein the means for modifying comprises means for setting the at least one sparse space coefficient to zero.

32. The apparatus of claim 23, wherein
the means for receiving is further configured to receive one or more packets comprising at least one of a corrupted version of the motion information or a corrupted version of the samples, and the apparatus further comprising
means for reconstructing at least one of the motion information or the samples using the one or more packets.

33. The apparatus of claim 23, wherein the means for determining the at least one sparse space coefficient further comprises:
means for identifying the at least one sparse space coefficient based on a priori statistical information about noise sources.

34. A computer-program product for signal processing, comprising a non-transitory computer-readable storage device encoded with instructions executable to:
receive samples of a signal from a sensor;
receive information related to a motion of the sensor;
generate a sparsity basis and a sensing matrix;
determine at least one sparse space coefficient by using the sensing matrix, the sparsity basis and the received samples;
modify the at least one sparse space coefficient based on the motion information to mitigate artifacts present in the at least one sparse space coefficient due to the motion of the sensor;
determine one or more other signals related to the received samples by using the at least one modified sparse space coefficient.

35. A headset, comprising:
a receiver configured to receive:
samples of a signal from a sensor;
information related to a motion of the sensor;
a first circuit configured to generate a sparsity basis and a sensing matrix;
a computer configured to determine at least one sparse space coefficient by using the sensing matrix, the sparsity basis and the received samples;
a second circuit configured to modify the at least one sparse space coefficient based on the motion information to mitigate artifacts present in the at least one sparse space coefficient due to the motion of the sensor;
an estimator configured to determine one or more other signals related to the received samples by using the at least one modified sparse space coefficient; and
a transducer configured to provide an audio output based on the determined one or more other signals.

36. A watch, comprising:
a receiver configured to receive:
samples of a signal from a sensor;
information related to a motion of the sensor;
a first circuit configured to generate a sparsity basis and a sensing matrix;
a computer configured to determine at least one sparse space coefficient by using the sensing matrix, the sparsity basis and the received samples;
a second circuit configured to modify the at least one sparse space coefficient based on the motion information to mitigate artifacts present in the at least one sparse space coefficient due to the motion of the sensor;
an estimator configured to determine one or more other signals related to the received samples by using the at least one modified sparse space coefficient; and
a user interface configured to provide an indication based on the determined one or more other signals.

37. A monitoring device, comprising:
a connector;
a receiver configured to receive via the connector:
samples of a signal from a sensor;
information related to a motion of the sensor;

a first circuit configured to generate a sparsity basis and a sensing matrix;

a computer configured to determine at least one sparse space coefficient by using the sensing matrix, the sparsity basis and the received samples;

a second circuit configured to modify the at least one sparse space coefficient based on the motion information to mitigate artifacts present in the at least one sparse space coefficient due to the motion of the sensor;

an estimator configured to determine one or more other signals related to the received samples by using the at least one modified sparse space coefficient; and a user interface configured to provide an indication based on the determined one or more other signals.

38. A method for signal processing, comprising:

receiving, by an apparatus, motion information and samples of a signal;

generating, by the apparatus, a sparsity basis and a sensing matrix;

determining, by the apparatus, at least one sparse space coefficient by using the sensing matrix, the sparsity basis and the received samples;

modifying, by the apparatus, the at least one sparse space coefficient based on the motion information;

determining, by the apparatus, one or more other signals related to the received samples by using the at least one modified sparse space coefficient;

generating, based on at least one of the determined one or more other signals or the motion information, feedback information for adjusting sensing at an apparatus of at least one of other samples of the signal or other motion information, the other samples and the other motion information to be received from the apparatus; and transmitting the generated feedback information to the apparatus, wherein the feedback information comprises at least one of: an update of an under-sampling ratio (USR) information about a lighting intensity of light-emitting diodes (LEDs), or a correction of DC component of the signal.

39. An apparatus for signal processing, comprising:

a receiver configured to receive motion information and samples of a signal;

a first circuit configured to generate a sparsity basis and a sensing matrix;

a computer configured to determine at least one sparse space coefficient by using the sensing matrix, the sparsity basis and the received samples;

a second circuit configured to modify the at least one sparse space coefficient based on the motion information;

an estimator configured to determine one or more other signals related to the received samples by using the at least one modified sparse space coefficient;

a third circuit configured to generate, based on at least one of the determined one or more other signals or the motion information, feedback information for adjusting sensing at another apparatus of at least one of other samples of the signal or other motion information, the other samples and the other motion information to be received from the other apparatus; and a transmitter configured to transmit the generated feedback information to the other apparatus, wherein the feedback information comprises at least one of: an update of an under-sampling ratio (USR) information about a lighting intensity of light-emitting diodes (LEDs), or a correction of DC component of the signal.

40. An apparatus for signal processing, comprising:

means for receiving motion information and samples of a signal;

means for generating a sparsity basis and a sensing matrix;

means for determining at least one sparse space coefficient by using the sensing matrix, the sparsity basis and the received samples;

means for modifying the at least one sparse space coefficient based on the motion information;

means for determining one or more other signals related to the received samples by using the at least one modified sparse space coefficient;

means for generating, based on at least one of the determined one or more other signals or the motion information, feedback information for adjusting sensing at another apparatus of at least one of other samples of the signal or other motion information, the other samples and the other motion information to be received from the other apparatus; and means for transmitting the generated feedback information to the other apparatus, wherein the feedback information comprises at least one of: an update of an under-sampling ratio (USR) information about a lighting intensity of light-emitting diodes (LEDs), or a correction of DC component of the signal.

* * * * *